US005690675A

United States Patent [19]
Sawyer et al.

[11] Patent Number: 5,690,675
[45] Date of Patent: Nov. 25, 1997

[54] METHODS FOR SEALING OF STAPLES AND OTHER FASTENERS IN TISSUE

[75] Inventors: Philip N. Sawyer, Brooklyn, N.Y.; Philip M. Sawyer, Menlo Park; Cary J. Reich, Laguna Hills, both of Calif.

[73] Assignee: Fusion Medical Technologies, Inc., Mountain View, Calif.

[21] Appl. No.: 481,712

[22] Filed: Jun. 7, 1995

Related U.S. Application Data

[63] Continuation-in-part of Ser. No. 303,336, Sep. 6, 1994, which is a continuation-in-part of Ser. No. 7,691, Jan. 22, 1993, abandoned, which is a continuation-in-part of Ser. No. 832,171, Feb. 6, 1992, abandoned, which is a continuation-in-part of Ser. No. 654,860, Feb. 13, 1991, Pat. No. 5,156,613.

[51] Int. Cl.$^6$ .................................................. A61B 17/00
[52] U.S. Cl. .................. 606/229; 606/27; 606/32; 606/213; 606/214; 606/228; 606/230; 128/898
[58] Field of Search ............ 424/400; 606/7, 606/8, 10, 12, 17, 213, 214, 40, 3, 215, 27, 32, 2, 228, 229, 230, 233; 128/898, DIG. 8; 607/1

[56] References Cited

U.S. PATENT DOCUMENTS

| | | | |
|---|---|---|---|
| 4,854,320 | 8/1989 | Dew et al. | 128/397 |
| 5,071,417 | 12/1991 | Sinofsky | 606/8 |
| 5,156,613 | 10/1992 | Sawyer | 606/213 |
| 5,209,776 | 5/1993 | Bass et al. | 106/124 |
| 5,503,638 | 4/1996 | Cooper et al. | 623/11 |

FOREIGN PATENT DOCUMENTS

| | | |
|---|---|---|
| 92/14513 | 3/1992 | WIPO . |
| 93/01758 | 4/1993 | WIPO . |

OTHER PUBLICATIONS

Oz, M. C. et al. SPIE vol. 1200, pp.55–59 (1990).
Joel D. Cooper, MD "Technique to Reduce Air Leaks After Resection of Emphysematous Lung," Ann Thorac Surg, 57:1038–1039. (1994).
Product Brochure, Peri–Strips™ for Staple Line Reinforcement, Bio–Vascular, Inc., two pages, Rev. 97003A (1994).
Product Brochure, Peri–Guard® Processed Bovine Pericardium, Bio–Vascular, six pages, 98501 Rev. A (1992).

*Primary Examiner*—Raj Bawa
*Attorney, Agent, or Firm*—Townsend and Townsend and Crew LLP

[57] ABSTRACT

Wounds in lung tissue are closed in a two step method consisting essentially of applying fasteners to a region adjacent to the wound, wherein the fasteners may cause penetrations. The fasteners are present in a preformed layer of collagen, fibrin, fibrinogen, elastin, albumin, or a combination thereof, and energy is applied to the region to fuse the material to the tissue and seal perforations in the tissue.

14 Claims, 4 Drawing Sheets

METHODS FOR SEALING OF STAPLES AND OTHER FASTENERS IN TISSUE

The present invention is a continuatton-in-part of application Ser. No. 08/303,336, filed on Sep. 6, 1994, which was a continuation-in-part of application Ser. No. 08/007,691, filed on Jan. 22, 1993, now abandoned, which was a continuation-in-part of application Ser. No. 07/832,171; filed on Feb. 6, 1992, now abandoned, which was a continuation-in-part of application Ser. No. 07/654,860, filed on Feb. 13, 1991, now U.S. Pat. No. 5,156,613. The present application claims the benefit of the filing date of application Ser. No. 08/303,336 only. The full disclosure of application Ser. No. 08/303,336, is incorporated herein by reference.

BACKGROUND OF THE INVENTION

1. Field of the Invention

The present invention relates generally to devices, articles, and methods for effecting and enhancing wound closure in tissue. More particularly, the present invention relates to the use of a fusible material together with fasteners for closing wounds, wherein energy is applied to the fusible material to seal the closure.

Chronic obstructive pulmonary diseases, such as emphysema and small airway diseases, affect from five to ten million people in the United States alone. In about ten percent of such cases, chronic alveolar inflammation is so severe that large portions of the lung are destroyed, resulting in greatly reduced oxygen exchange and significant breathing difficulties. Such cases can result in partial or complete disability, and in the worst cases death.

One procedure for treating advanced chronic obstructive pulmonary disease, referred to as a bullectomy or lung tailoring, involves the surgical excision of diseased lung tissue and suturing to close the lung along the excision line. Surgical resection of lung tissue is also performed for volume reduction, blebectomies, segmentectomies, lobectomies, wedge resections, bronchial resections, pneumonectomies, and pneumoreductions. Unfortunately, lung tissue is extremely fragile (particularly when weakened by diseases such as emphysema) and does not hold sutures well. The needle holes resulting from suturing can result in lung perforations which leak large amounts of air. Such post-operative air leaks often require long hospital stays and result in a high morbidity rate for the procedures. For these reasons, bullectomies where the lung is closed by suturing are seldom performed at present.

The prognosis for bullectomy procedures has been significantly improved by the introduction of modern surgical stapling techniques. Multiple row linear staplers have been used to both cut and close diseased lung tissue in both wedge resection and lobectomy procedures. Further improvement in such staple bullectomy procedures has been reported with the use of bovine pericardial strips to buttress and reinforce the staple line used to close the lung along the resection edge.

Although a significant improvement over prior procedures, the use of pericardium-reinforced stapling techniques during lung resection procedures is still problematic. The staple holes in the pericardial strips can still present small lung perforations, particularly when the strip is under pressure. Even very small perforations can result in air leakage as high as 2–5 liters/min. Moreover, the pericardial strips are not uniformly secured to the underlying lung tissue, and the terminal and side edges of the strip can separate from and/or tear the adjoining tissue, further contributing to air leakage. In particular, since the pericardial strips are attached to the underlying tissue only by the staples, air can leak from the staple perforations or elsewhere outward past the edges of the strip, i.e., pericardial strips do not seal the tissue closure in any significant way. Additionally, the use of bovine pericardial strips does not appear to promote healing of the underlying lung tissue, and particularly does not appear to promote fibroblast ingrowth to seal lung perforations which may be present after the procedure. Finally, present procedures do not provide for sealing or patching diseased areas of the lung other than by excising the diseased tissue and sealing along the excision line with staples with or without a pericardium patch. It would thus be desirable to provide procedures where diseased lung tissue could be sealed to prevent air leakage without the need to excise tissue.

2. Description of the Background Art

The use of bovine pericardial strips to reinforce lung staple lines in performing bullectomies for treating emphysema is described in Cooper (1994) *Ann. Thorac. Surg.* 57:1038–1039. Bovine pericardial strips of the type utilized for staple line reinforcement are commercially available from Bio-Vascular, Inc., St. Paul, Minn., under the trade name Peri-Strips™. U S. Pat. No. 5,156,613, PCT Application WO 92/14513, and copending application Ser. No. 08/231,998, assigned to the assignee of the present invention, describe a method for joining or reconstructing tissue by applying energy to a tissue site in the presence of a collagen filler material. Copending application Ser. No. 08/370,552, describes the use of an inert gas beam energy source for fusing collagen and other materials to tissue for joining or reconstructing the tissue. U.S. Pat. No. 5,071,417, describes the application of laser energy to biological materials to seal anastomoses. U.S. Pat. No. 5,209,776, describes protein materials which may be activated with energy and bonded to tissue. PCT Application WO 93/01758 describes an argon beam coagulator for treating tissue.

SUMMARY OF THE INVENTION

The present invention provides improved methods and devices for closing wounds in tissue using fasteners, such as staples, pins, hooks, sutures, and the like. The fasteners are applied to tissue in a conventional manner to close the wound, and energy is applied thereafter to a material disposed in a region over an adjacent wound which (upon application of the energy) fuses to the tissue to enhance the wound closure and seal perforations which may be present in the region due to fastener placement or other causes.

The fusible material is a biologic or biocompatible synthetic substance which will bond to underlying tissue upon application of energy from a suitable source, as described in more detail hereinafter. Preferred is the use of biological materials, such as proteins and protein-containing mixtures, which will bond to tissue proteins (e.g. covalently, non-covalently, physically, and combinations thereof) upon application of suitable activating energy. Exemplary biological materials include collagen, gelatin, elastin, fibrinogen, fibrin, albumin, and composites and mixtures thereof.

The fusible material may be applied to the wound region as a solid phase or as a non-solid dispersible phase. By "solid phase," it is meant that the fusible material is formed as a sheet, layer, film, strip, patch, mesh, or the like, over the wound region. By "non-solid dispersible phase," it is meant that the fusible material is in the form of a liquid, gel, powder, or combinations thereof, which may be spread, sprayed, painted, or otherwise dispersed over the wound region. Regardless of its initial state, the fusible material will be in the form of a solid or gel layer after energy has been applied according to the method of the present invention. That is, solid sheets, layers, films, strips, patches, and the like, will remain as a solid (although the dimensions may alter slightly as the material is softened and fused to the underlying tissue) while meshes and non-solids will be converted into solid or gel layers.

The fusible material may be applied before, during, or after placement of the fasteners, and is preferably applied together with the fasteners as a backing or reinforcement layer, where the fusible material is initially held in place by the fasteners and subsequently fused to the underlying tissue upon the application of energy. Such procedures are particularly advantageous since they require only two steps, i.e., the simultaneous placement of fastener and fusible material followed by the application of energy to fuse the material to tissue and enhance the tissue closure by sealing any perforations which may have resulted from the prior placement of the fasteners (as described above).

Optionally, the solid phase forms of the fusible material, such as sheets, layers, films, strips, and patches, may be reinforced with non-fusible materials to increase their strength and enhance their use as backings during the initial placement of the fasteners, particularly staples. Usually, the non-fusible materials will also be non-bioabsorbable so that the reinforcement material can remain in place to support the staples or other fasteners indefinitely. Exemplary reinforcement materials include meshes or braids composed of polymeric materials.

The methods of the present invention can rely on the application of energy from a wide variety of sources, including radiofrequency (RF) energy, laser energy, ultraviolet energy, ultrasonic energy, and the like. Preferred is the use of RF energy which can be provided by conventional electrosurgical power supplies operating at frequencies in the range from 200 kHz to 1.2. MHz. Particularly preferred is the use of RF energy applicators which provide a uniform, dispersed energy flux over a defined area, such as inert gas beam RF energy sources, more particularly argon beam RF energy sources. Standard electrocautery devices could also find use.

In the exemplary embodiment, the methods and devices of the present invention are used to enhance sealing of lung tissue in lung resection procedures where lung tissue has been removed along an excision line. Typically, the lung tissue is excised and closed using a conventional multiple row, linear stapler. The fusible material is applied as a backing or reinforcement layer with the staples, preferably being placed on or over the stapler head and/or anvil prior to stapling. The solid layer of fusible material thus acts as a mechanical support for the staples as they are initially placed in the fragile lung tissue. In addition to such initial mechanical support, however, the present invention provides for subsequent sealing of the lung tissue along and around the staple line by application of energy to the wound region to initiate fusion of the material to the underlying lung tissue. Fusion of the material effects sealing of perforations in the wound region which may be due to the initial stapling or other causes. In particular, sealing of the fusible material to the underlying tissue over regions adjacent to all sides of the staple line will inhibit or prevent leakage past the edges of the solid layer of fusible material which is formed. Additionally, fusing of the backing layer will provide "stress relief" to permit realignment of the individual staples to reduce tearing and damage to the lung tissue as the lung expands and contracts during respiration.

DESCRIPTION OF THE SPECIFIC EMBODIMENTS

Figure 1:
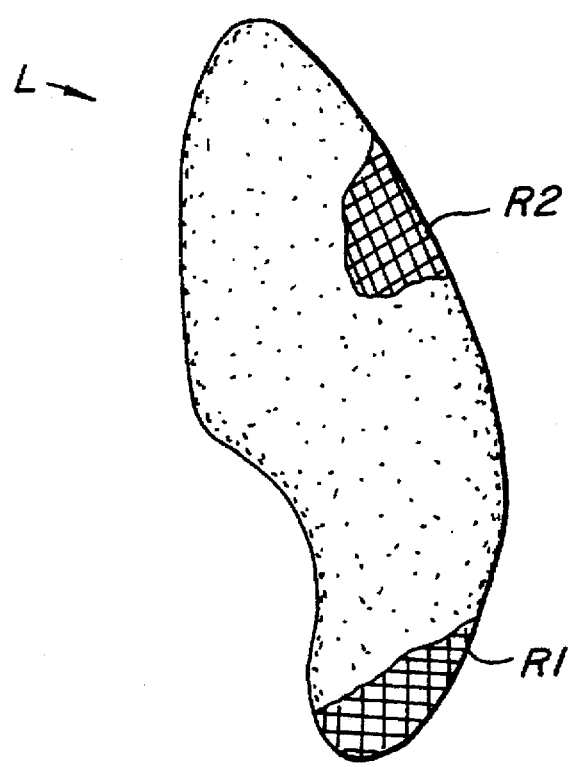
FIG. 1 is a schematic illustration of a lung having diseased tissue regions.

Methods and devices according to the present invention may be used for closing wounds in virtually any body tissue, and are particularly useful for closing wounds in the tissue of fragile body organs, such as lungs, stomach, liver, spleen, intestines, colon, and the like. The wounds may result from accidental trauma, surgical intervention, or virtually any other cause, with the methods and devices being particularly useful for the closure of surgical resections made in the lungs (lung volume reductions, bullectomies, lobectomies, segmentectomies, bronchial resections, wedge resections, pneumonectomies, pneumoreductions, etc.), in the gastrointestinal tract, (gastrectomies, intestinal/colon resection), in the liver, and in the spleen. The present invention provides both secure mechanical closure of the wound and prevention or inhibition of fluid leakage, including both air leakage and liquid fluid leakage, such as blood and other bodily fluids. The present invention is particularly suitable for performing lung resections where the remaining portion of the lung is closed and sealed along the resection line.

The present invention relies on the use of conventional surgical fasteners for initial closing of the wound. Exemplary fasteners include suture, staples, clips, pins, hooks, and the like. The present invention is particularly useful with surgical stapling devices, such as multiple row, in-line staplers of the type available from U.S. Surgical Corp., Norwalk, Conn., and Ethicon, Inc., Somerville, N.J., including both disposable and reusable devices, such as those devices intended for use in laparoscopic procedures.

The present invention particularly relies on applying a fusible material to the region on the outer tissue surface surrounding the wound, where the fusible material may penetrate at least to some extent to the inner wound surfaces that are being joined by the procedure. The fasteners used in the primary closure of the wound penetrations will usually cause perforations in the tissue surrounding the wound as the mechanical closure is effected. The presence of the fasteners in the penetrations will often impart some stress to the tissue, where the stress in turn can result in enlargement of the penetration(s). This is a particular problem with staple closures of the lung, where lung inflation during respiration can place significant stress on the lung tissue, especially at the edges of the resection line, causing the staples to enlarge the penetrations and permit significant air loss, as described previously. Stress can also concentrate at the edge of conventional pericardial patches, which in turn can tear lung tissue and cause air leakage. The fusible materials of the present invention (which upon application of energy bond and seal to the underlying tissue) can act to seal such perforations and enlarged penetrations and thus enhance the mechanical integrity of the wound closure. Moreover, solid sheets of fusible materials may be used as a backing or reinforcement layer to help anchor staples and other fasteners during initial placement of the fasteners prior to fusing.

The fusible material may be any natural, modified natural, or synthetic substance which has the ability to be applied over the wound region in a solid or non-solid state, and thereafter to be fused to the underlying tissue surrounding the closed wound upon the application of energy from a suitable energy source. Thus, the fusible material will be able to create and/or maintain a solid, continuous film over (and sometimes penetrating into) the wound region to act both to mechanically enhance the wound closure and/or seal any perforations which may be present in the region. Such fusible materials should also be biocompatible (e.g., should be non-immunogenic and non-inflammatory), and usually (but not necessarily) will be bioabsorbable overtime (e.g., being partially or completely resorbed into the underlying tissue over a period from 1 day to 90 days. Suitable synthetic materials include organic polymer films which contain or have been modified to contain side groups which will bond (covalently or hydrostatically) or otherwise adhere to the underlying tissue. Exemplary synthetic materials suitable for use in the present invention include organic polymers such as poly(lactic acid), poly(glycolic acid), poly(hydroxybutyrate), poly(phosphazine), polyester, and the like.

Generally, the use of natural biological polymers, and in particular biological proteins, is preferred. Suitable proteins include collagen, fibrin, fibrinogen, elastin, albumin, combinations thereof, and the like, and mixtures and derivatives thereof. Particularly preferred is the use of collagen and modified collagens, such as gelatin (which is a protein-containing material obtained by hydrolysis of collagen in a well known manner), as described in parent application Ser. No. 08/303,336, filed on Sep. 9, 1994, the full disclosure of which has been previously incorporated herein by reference. The fusible material will usually be applied to the wound region as a solid layer, e.g., in the form of a film, sheet, patch, strip, mesh, or the like. Use of a mesh allows tissue to form a coagulum within the interstices of the mesh as energy is applied, as described in patent application Ser. No. 08/303,336, the disclosure of which has been incorporated herein by reference.

The solid phase forms of the fusible material may optionally be reinforced with filaments, braids, meshes, and other woven and non-woven reinforcement materials. Preferably, the reinforcement materials will be non-bioabsorbable so that they will remain even after the fusible material has been resorbed. Thus, the reinforcement materials will remain to provide support for the fasteners over extended periods of time. Preferred reinforcement materials will be in the form of polymeric braids or meshes, particularly composed of polypropylene (Marlex®), fluoronated polymers (Gore-Tex®), and the like.

The solid phase forms of the fusible material may be formed by a variety of methods as described in copending application Ser. No. 08/303,336, the full disclosure of which has previously been incorporated herein by reference. Reinforcement materials can be added by various known techniques, such as impregnation, dipping, casting, co-extrusion, and the like.

Alternatively, the fusible material may be applied to the wound region in a non-solid dispersible state, e.g., as a liquid, gel, sol, paste, spray, or combination thereof. In the preferred solid layer form, the fusible material will be cut or trimmed into a desired shape prior to application to the wound region. Application to the wound region may occur before, during, or after application of the primary fasteners. In a particularly preferred embodiment, as described below, the fusible material will be applied to the tissue as a backing layer for the staples which are used as primary fasteners. Non-solid dispersible fusible materials may be applied using syringes, brushes, sprayers, spatulas, or other methods suitable for spreading or dispersing a thin layer of material over the wound region. In all cases, after application of the fusion energy, the fusible material will be in the form of a continuous solid film or gel over the wound region. That is, fusible materials which are originally in a solid, layer form will remain as a solid film, although the film will become bound to the underlying tissue and may alter in shape to some degree. In the case of non-solid and other discontinuous phases, the fusible material will be converted into a solid or gelatinous phase upon the application of energy. In the case of a fusible material which is applied in the form of a mesh, the application of energy will usually form a coagulum of tissue within the interstices of the mesh, resulting in a solid or gelatinous, continuous film comprising both the fusible material and the tissue coagulum after the energy has been applied.

In addition to the substances described above, the fusible material of the present invention may further include dyes, pigments, and the like, which affect the energy absorption of the material in some desired manner. For example, particular dyes may be added to enhance absorption of energy from the selected energy source. Additionally, dyes and pigments may be added simply to improve visualization of the material during use and/or permit materials having different characteristics to be distinguished from each other. Other substances and additives may be included with the fusible material for other purposes, as generally described in Parent application Ser. No. 08/303,336, filed on Sep. 9, 1994, the full disclosure of which has previously been incorporated herein by reference.

Other substances suitable for use as a component in the fusible material include glycosaminoglycans, such as hyaluronic acid, dermatan sulfate, chondroitin sulfate, and heparin. Use of the glycosaminoglycans is desirable since such materials, which are anti-thrombotics, can reduce adhesion to adjacent tissues and organs after the final solid or gelatinous layer has been formed by the application of energy.

The solid, forms of the fusible material will typically be provided as sheets, strips, films, or patches having a thickness sufficient to provide mechanical integrity both before and after application to the wound region. For most of the materials described above, and in particular for the collagen and gelatin materials, a thickness in the range from about 0.01 mm (0.5 mils) to 0.75 mm (30 mils), with a preferred thickness from 0.04 mm (1 mil) to 0.1 mm (4 mils) is suitable. Fusible materials having thicknesses generally greater than this range are less suitable since they have poor energy absorption characteristics and display increasing stiffness. Energy absorption and conduction within patches in the upper region of this range, from 0.1 mm to 0.75 mm, can be improved by the formation of holes partially or fully through the thickness of the material (referred to as "interlock vias" in Parent application Ser. No. 08/303,336, the full disclosure of which has previously been incorporated herein by reference). The peripheral dimensions of the continuous, solid sheets of fusible material are not critical. The sheets will typically be cut or trimmed to have a desired peripheral shape prior to use in the methods in the present invention. In a particularly preferred example, as described in more detail below, the sheets of fusible material may be formed into tubes, sleeves, or strips, which can be aligned along or over the heads and/or anvils of stapling devices, so that the materials will act as backing or reinforcement layers as the staples are applied to close the wound.

The method of the present invention will utilize energy of a type and in an amount sufficient to fuse the fusible material to underlying tissue. Suitable energy sources include electrical energy, particularly RF energy sources, heat energy, laser energy, ultrasonic energy, and the like. Preferred are the use of RF energy sources, such as those available as electrosurgical power supplies from companies such as Valleylab, Boulder, Colo., and Birtcher Medical Systems, Irvine, Calif., employing conventional RF-applying probes. Particularly preferred are modified radio frequency energy sources which provide for a dispersed or distributed current flow from a hand-held probe to the tissue. One such radio frequency energy source referred to as an inert gas beam coagulator which relies on flow of an inert ionizable gas, such as argon, for conducting current from the probe to the tissue.

Energy from the energy source will typically be manually directed to the tissue using a probe connected to an external power supply. The treating physician will manually direct the probe to apply energy over the surface of the fusible material and will visually confirm that fusion has been achieved. The probe may use conventional electrosurgical power supplies having an energy output from 2 W to 100 W, preferably from 20 W to 40 W. The fusible material will typically be exposed to the energy for a total time from about 5 seconds to 120 seconds, usually from 30 seconds to 40 seconds, for material having an area from 1 cm$^2$ to 10 cm$^2$. The precise timing will depend on the physician's visual assessment that fusion of the material to the underlying tissue has been achieved.

Referring now to FIG. 1, a lung L includes diseased regions R1 and R2. The diseased regions comprise giant bullae which are collapsing the adjoining gas-exchanging lung tissue. The methods and devices of the present invention may be advantageously used to resect such diseased regions R1 and R2 from the lung L and to further provide secure, generally air-tight seals along the resection lines.

Figure 2A:
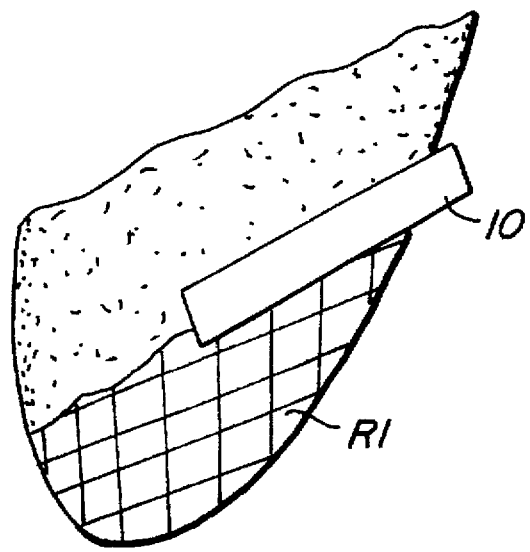
FIGS. 2A–2E illustrate a method according to the principles of the present invention where a strip of fusible material is placed along an excision line prior to stapling and excision using a conventional stapling apparatus.
Figure 2B:
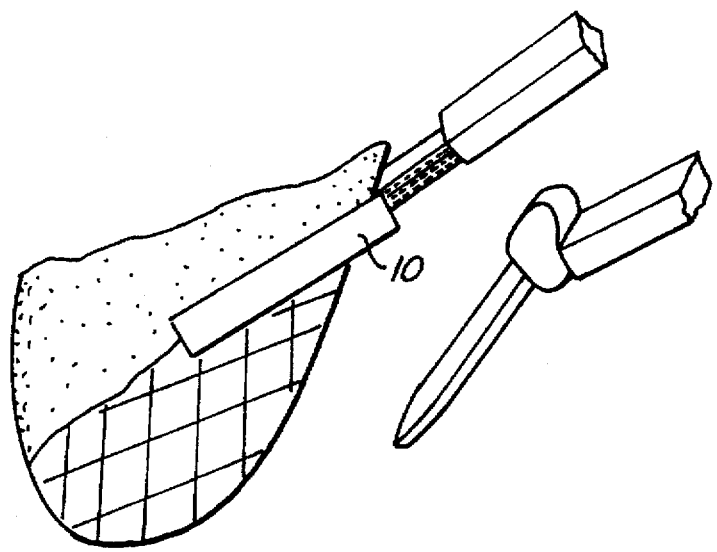
Figure 2C:
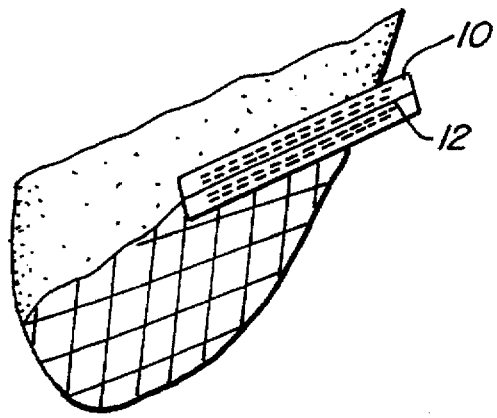
Figure 2D:
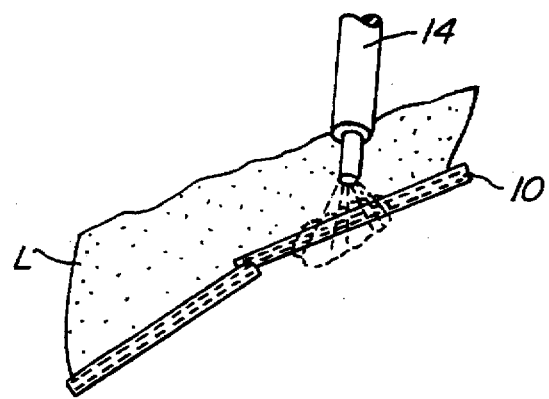

Referring now to FIGS. 2A–2E, diseased region R1 can be removed by applying a strip of fusible material 10 along the desired resection line, as illustrated in FIG. 2A. Preferably, a second strip will be provided on the opposite side of the lung, where the two strips are aligned prior to stapling, as shown in FIG. 2B. A conventional multiple row, in-line stapling device having an axial cutting blade disposed between a pair of double staple lines is shown in FIG. 2B. The stapler is applied over the opposed pair of fusible material strips 10, and the strips stapled together to form a sandwich along the desired section line, as shown in FIG. 2C. It will be appreciated that the tissue (as well as the fusible strips 10) have been cut along line 12 after the stapling operation. A second pair of fusible strips are then placed along the remaining length of the desired recision line, and the stapling and recision step repeated using the same stapler having a new stapling cartridge. After the resected tissue is removed, energy is applied over the fusible material strips 10 and adjacent tissue area, typically using an inert gas beam coagulator 14 as shown in FIG. 2D.

Figure 2E:
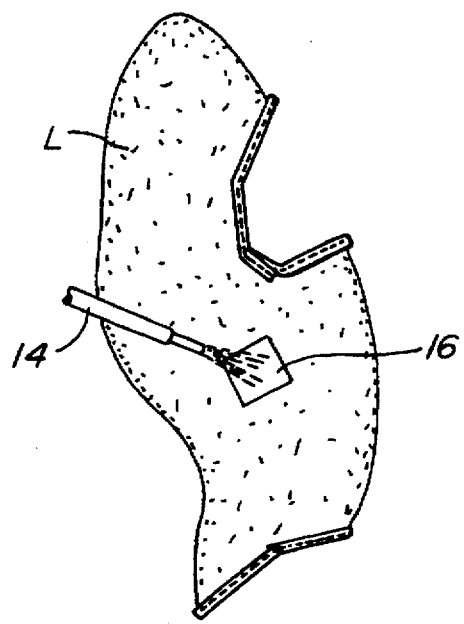

Similar patching, stapling, and resecting steps are taken to remove the second diseased region R2, as shown in FIG. 2E.

The method of the present invention is particularly useful since it also allows surface defects in the lung L to be corrected using patches 16, as also shown in FIG. 2E. The patch 16 can be cut to a desired size and geometry and placed over the lung defect. After placement, the inert gas beam coagulator 14 can be used to fuse the patch 16 to the lung tissue. At the end of the procedure, the diseased regions R1 and R2 have been removed, with the resulting resection lines sealed. Additionally, any surface defects in the lung L have been patched without tissue resection. Thus, the lung has been surgically repaired with the likelihood of perforations leading to air leaks being greatly reduced.

In order to enhance the integrity of the seal provided by tissue strips 10, it will generally be desirable to overlap the ends of multiple strips which are used in-line. Additionally, the strips 10 should extend beyond the resection line by a distance of at least 3 mm, preferably at least about 10 mm. In this way, a continuous sealing layer may be formed over all regions of the tissue which are at the greatest risk of air leakage.

Figure 3:
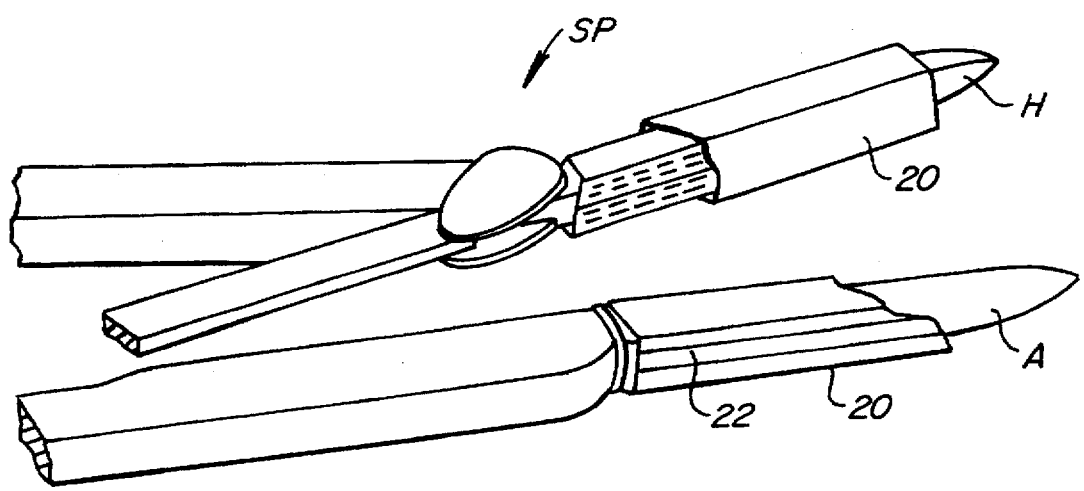
FIG. 3 illustrates a conventional stapling apparatus having a sleeve of fusible material disposed over the head and anvil.

In a preferred aspect of the present invention, the strips of fusible material may be initially placed over the head and/or anvil of a stapling device SD, as shown in FIG. 3. Preferably, sleeves 20 of the fusible material are wrapped around each of the anvil A and stapling head H, and secured by a strip of tape 22. The sleeves may be wrapped around the anvil head immediately prior to use, or preferably may be pre-formed and made available in a sterile package, where the physician may remove the sleeves immediately prior to use and place them over the stapling head. The sleeves may be provided in long, continuous lengths which may be cut into shorter segments having a desired length intended to fit over commercially available staplers, e.g., 50 mm, 55 mm, 65 mm, etc. The stapler may then be used to perform the method illustrated in FIGS. 2A–2E, except that there is no need to manually place strips of 10 of the fusible material prior to stapling. After stapling using the stapling device SD as shown in FIG. 3, the stapling head and anvil are separated from the cut sleeves 20, and the sleeve material may be trimmed to a desired width and geometry prior to the application of energy.

Figure 4A:
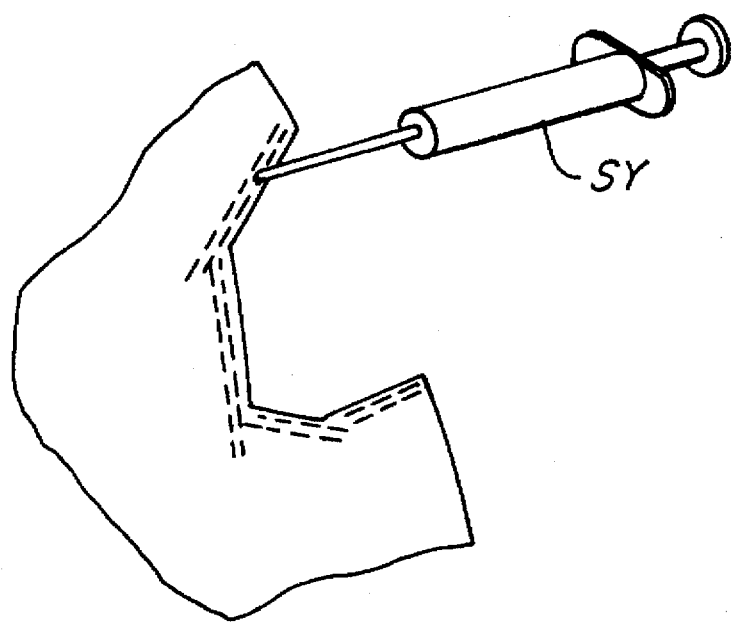
FIGS. 4A and 4B illustrate an alternative method according to the present invention for excising and sealing diseased lung tissue, where the diseased tissue is first excised and stapled and a non-solid fusible material then applied over the stapled region prior to applying energy.
Figure 4B:
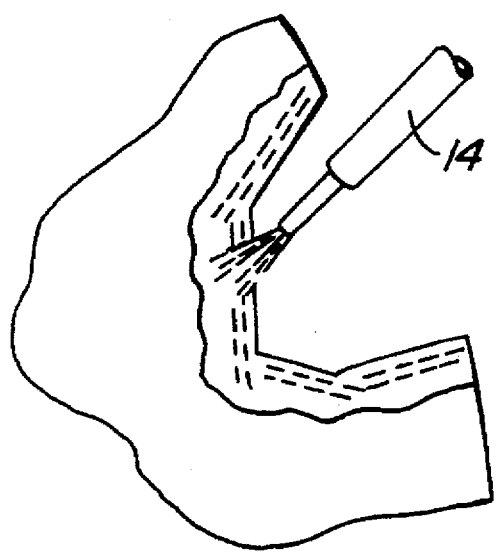

Liquid, gel, and other non-solid forms of the fusible material may be applied in a variety of manners. For example, a syringe SY may be used to apply a liquid fusible material over a wound region which has previously been stapled, as shown in FIG. 4A. The material may be applied, and optionally spread using a spatula or the like, and the fusion energy then applied using any of the sources described above, such as the inert gas beam coagulator 14 described previously. After application of energy, the fusible material will be in the form of a thin, continuous film of the material to protect and seal the wound region.

The following examples are offered by way of illustration, not by way of limitation.

EXPERIMENTAL

Materials and Methods

1. Filtered Collagen Patch Preparation

Fibrous bovine corium collagen (Kensey-Nash Semed F collagen, Kensey-Nash Corporation, Exton, Pa.) was dispersed in distilled water at 10% solids (w/v). Polyethylene glycol 400 MW (PEG, U.S.P. or pharmaceutical grade) was also added to 1% solids (w/v). The dispersion was heated at 70° C. for 50 minutes with occasional agitation. The dispersion was then filtered through a 100 micron mesh. The filtrate was analyzed for percent solids and was adjusted to 4% solids (including PEG) by addition of distilled water. During the filtration and dilution steps, the filtrate was maintained at temperatures >35° C. to prevent gelling of the filtrate. The filtrate was poured into dishes to form gels. To achieve the desired final patch thickness, 13 ml was poured into polystyrene petri dishes (100×100×15 mm, Baxter Scientific Products, McGaw Park, Ill.) and allowed to gel at room temperature (20°–24° C.). To achieve a patch which is uniform in thickness, the poured filtrate and dish was maintained level. The poured filtrate gelled within 30 minutes, and the gel was allowed to dry at ambient conditions. Patches were dried until the moisture content reached 10–14%(w/w). Moisture levels below 10% were undesirable, since patches could become brittle. Dried films were freed from dishes and cross-linked with UV light; 254 nm at 4.4 watts/cm$^2$ for 20–40 minutes (Model UVC-515 Ultraviolet Multi-linker, Ultra-Lum, Inc., Carson, Calif.). Patches were sterilized by placing in heat-sealed polyester barrier pouches, or equivalent moisture barrier enclosures, and irradiating with electron beam at 2.5–3.0 megarads (Nutek Corporation, Palo Alto, Calif.). The final dried, cross-linked patch was 0.04–0.06 mm thick, contained 8–20% PEG (w/w), with the remainder being cross-linked annealed gelatin. The melting temperature of the fully hydrated patch (hydrated in 0.1%aq. NaCl) by differential scanning calorimetry (DSC, Thermal Analyst 2100). TA Instruments, New Castle, Del.) was 34°–40° C. (heating rate 10° C./min). Native collagen, which has a fully helical structure, melts at 50°–70° C. under the same conditions.

2. Granular Collagen Patch Preparation

Fibrous bovine collagen was dispersed in distilled water at 3.3–3.8%(w/v), with 0.3%(w/v) PEG 400 MW, and heated as in the filtered formulation. After 50 min at 70° C., the dispersion was circulated through a homogenizer (Virtis Cyclone IQ$^2$, fitted with 20 mm diameter rotor-stator with flow-through head, containing slotted orifices with approximately 1 mm gap, operated at 20,000 rpm; net fluid flow through the head :150 ml/min, controlled by a pump external to the homogenizer; two complete passes through the homogenizer). Microscopic inspection of the collagen after heating and homogenization showed that all fibrous clumps were broken up. The homogenized dispersion was then poured into dishes (total protein solids 3.3–3.8%, w/v), gelled, dried, cross-linked, and sterilized as in the filtered patch formulation. These patches were 0.07–0.10 mm thick, due to the size of the fibers which are dried into the film. They were more opaque than the filtered formulation. DSC melting temperatures were 35° to 40° C.

3. Gelatin Patch Formulation

Pharmaceutical grade gelatin, from bovine or porcine source (300 Bloom, Dynagel, Inc., Calumet City, Ill., or Hormel Foods Corp., Austin, Minn.) was dissolved at 3.3 to 3.8% (w/v) in distilled water, along with 0.3% PEG 400 MW (w/v), by heating 3–5 minutes at 50°–60° C. with stirring. The dissolved gelatin was cast into gels, dried, cross-linked, and sterilized as in the filtered patch formulation. These patches were 0.04 to 0.06 mm thick and almost transparent; DSC melting temperatures were 33°–38° C.

4. RF Energy Source

Radio frequency current was supplied by a Birtcher 6400 Argon Beam Coagulator equipped with a triple control hand piece (3:1 probe). Energy was applied at 40 W with an Argon flow of 4 liters/min.

5. Procedure

A pig (60 kg) was anesthetized, intubated, and prepared for a thoracotomy. A right thoracotomy was made through the fourth interspace, and a substantial portion of both the upper and lower lobes of the lung was exposed.

A 55 mm Ethicon Proximate Linear Cutter (Ethicon, Inc., Sommerville, N.J.) stapler was used to staple several locations in the lung, including (1) the lingula of the upper lobe, (2) the apex of the lower lobe, (3) the inferior aspect of the lower lobe which provided a relatively long 10 cm stapling site, and (4) a wedged-out segment of the lung. The filtered collagen patch, the granular patch, and the gelatin patch were each used for reinforcing the staple line applied to the lung.

Sheets of the filtered collagen patch, the granular patch, and the gelatin patch were placed over the stapler head and anvil prior to use. In both cases, the patch material was wrapped around the stapler head or anvil and secured as a tubular sleeve thereover by adhesive steri strips. The staples and the reinforcement patches were then applied to the lung tissue simultaneously in a single stapling and resection operation. After stapling was complete, the reinforcement patches were cut from the stapler head and anvil, trimmed and welded to the underlying lung tissue using the RF argon beam coagulator.

Results

The filtered collagen patch material the granular patch material, and the gelatin patch material were used successfully in the staple line reinforcement procedures. Each of the patch materials readily formed a tube which was easily wrapped around the stapler head/anvil. It appears that each of the filtered collagen, granular collagen, and gelatin welding patch materials can be formed as a cylindrical tube without the need to utilize external tapes or other closing devices. When initially stapled in place, prior to application of the RF energy, each of the reinforcement materials provided a strong buttress without cracking.

After fusion to the underlying tissue, no leaks were observed in the region surrounding the staples and/or fused patch material. Welding of the collagen and gelatin materials was particularly useful in preventing leakage at the axial ends of the patches. These patches further acted to prevent bleeding.

Although the foregoing invention has been described in detail for purposes of clarity of understanding, it will be obvious that certain modifications may be practiced within the scope of the appended claims.

What is claimed is:

1. A method for closing a wound in tissue, said method consisting essentially of the following two steps performed sequentially:

applying fasteners selected from the group consisting of staples, clips, pins, hooks, and suture to a region adjacent to the wound to close the wound, wherein the fasteners cause penetrations in the tissue and the fasteners are present in a preformed layer of a material selected from the group consisting of collagen, fibrin, fibrinogen, elastin, albumin, and combinations, thereof, which fuses to the tissue upon the application of energy; and applying energy selected from the heat, radiofrequency, laser, ultrasonic, and electrical energy to the region to fuse the material to the tissue and seal perforations in the tissue.

2. A method as in claim 1, wherein the layer comprises a solid or mesh layer.

3. A method as in claim 1, wherein the performed sheet has peripheral dimensions corresponding to the wound region.

4. A method as in claim 1, wherein the applied energy is selected from the group consisting of radio frequency energy, heat energy, laser energy, and ultrasonic energy.

5. A method as in claim 4 wherein the energy applying step comprises directing energy from a radio frequency inert gas coagulator applicator against the wound region.

6. A method as in claim 1, wherein the material comprises gelatin and the energy is applied at a level from 1 W/cm$^2$ to 100 W/cm$^2$ to fuse to the tissue without substantial loss of mechanical strength.

7. A method as in claim 1, wherein the fasteners are staples and applying the fasteners comprises simultaneously placing multiple staple lines with a stapler.

8. A method as in claim 1, wherein the material is a reinforced solid, wherein the reinforcement is composed of a non-bioabsorbable material.

9. A method for sealing a resection line in lung tissue, said method consisting essentially of the following two steps performed sequentially:

applying along the resection line fasteners selected from the group consisting of staples, clips, pins, hooks, and suture to close the lung tissue, wherein the fasteners are present in a preformed layer of a material selected from the group consisting of collagen, fibrin, fibrinogen, elastin, albumin, and combinations thereof, which fuses to the lung tissue upon the application of energy; and applying energy selected from the heat, radiofrequency, laser, ultrasonic, and electrical enerqy to the region to fuse the material to the tissue and seal perforations in the tissue.

10. A method as in claim 9, wherein the fastener applying step is performed with an in-line stapler having a cutting blade disposed adjacent to a multiple staple line.

11. A method as in claim 9, wherein the applied energy is selected from the group consisting of radio frequency energy, heat energy, laser energy, and ultrasonic energy.

12. A method as in claim 1, wherein the energy applying step comprises directing energy from a radio frequency inert gas coagulator applicator against the material covering the wound region.

13. A method as in claim 9, wherein the material comprises gelatin and the energy is applied at a level from 1 W/ to 100 W/ to fuse to the tissue without substantial loss of mechanical strength.

14. A method as in claim 9, wherein the material is a reinforced solid, wherein the reinforcement is composed of a non-bioabsorbable material.

* * * * *